United States Patent [19]

Crowley et al.

[11] Patent Number: 5,151,355

[45] Date of Patent: Sep. 29, 1992

[54] PROCESS FOR THE PRODUCTION OF HIGH PURITY THROMBIN

[75] Inventors: Carmel Crowley, Dundrum; Timothy G. Sheehan, Ballincollig; Frederick G. Ward, Kilpedder, all of Ireland

[73] Assignee: Warner Lambert Pottery Road Limited, Dun Laoghaire, Ireland

[21] Appl. No.: 644,800

[22] Filed: Jan. 23, 1991

[30] Foreign Application Priority Data

Jan. 24, 1990 [IE] Ireland .................. 266/90

[51] Int. Cl.$^5$ .................. C12N 9/74; A61K 37/547
[52] U.S. Cl. .................. 435/214; 424/94.64
[58] Field of Search .................. 435/214; 424/94.64

[56] References Cited

U.S. PATENT DOCUMENTS

| | | | |
|---|---|---|---|
| 4,286,056 | 8/1981 | Andary et al. | 435/214 |
| 4,363,319 | 12/1982 | Altshuler | 435/214 |
| 4,380,511 | 4/1983 | Mannuzza et al. | 435/214 |
| 4,470,969 | 9/1984 | Pancham et al. | 530/831 |
| 4,473,553 | 9/1984 | Zuffi et al. | 530/831 |
| 4,637,932 | 1/1987 | Pancham | 530/831 |
| 4,696,812 | 9/1987 | Silbering et al. | 424/445 |
| 4,736,018 | 4/1988 | Reutelingspurger | 530/412 |
| 4,965,203 | 10/1990 | Silbering et al. | 435/188 |

FOREIGN PATENT DOCUMENTS

| | | | |
|---|---|---|---|
| 265329 | 3/1989 | Fed. Rep. of Germany | 435/214 |
| 1527261 | 12/1989 | U.S.S.R. | 435/214 |

*Primary Examiner*—David M. Naff
*Assistant Examiner*—Mike Meller
*Attorney, Agent, or Firm*—Ronald A. Daignault

[57] ABSTRACT

A liquid thrombin preparation is prepared by reacting a unit of prothrombin with less than 5 units of thromboplastin in the presence of calcium, contacting the resultant thrombin with a phosphate buffer, and diluting and filtering the suspension. The filtrate is then applied sequentially to an anion-exchange agarose column and a cation-exchange agarose column and the thrombin fraction is step-wise eluted from the latter column with phosphate buffered saline. Liquid thrombin preparations thereby obtained have specific activities greater than 1,600 U/mg and can be used in haemostasis.

8 Claims, 8 Drawing Sheets

PROCESS FOR THE PRODUCTION OF HIGH PURITY THROMBIN

BACKGROUND OF THE INVENTION

1. Field of the Invention

This invention relates to the production of thrombin, thrombin preparations thereby produced and their application in haemostasis.

Thrombin is a proteolytic enzyme, derived from prothrombin, which converts fibrinogen to fibrin. During the normal clotting of blood the insoluble protein fibrin is formed from fibrinogen by the proteolytic action of thrombin. Blood clots are formed to a large extent of fibrin.

2. Description of the Prior Art

Preparations of both bovine and human thrombin have been used in haemostasis. Preparations of bovine thrombin are currently used topically to control haemorrage from puncture sites or from capillary oozing in surgery. Thrombin (USP) is a sterile freeze-dried powder containing the protein obtained from bovine prothrombin and contains calcium. Freeze-dried thrombin preparations are sold under the Trade Mark THROMBOSTAT marketed by Parke Davis. Liquid thrombin preparations are also known and are the subject of U.S. Pat. Nos. 4,696,812 and 4,965,203. Liquid thrombin preparations are generally favoured in that they require no reconstitution prior to use and can be sold in ready-to-use form. Special buffer systems have been used to provide the stable thrombin compositions of U.S. Pat. Nos. 4,696,812 and 4,965,203.

Figure 1:
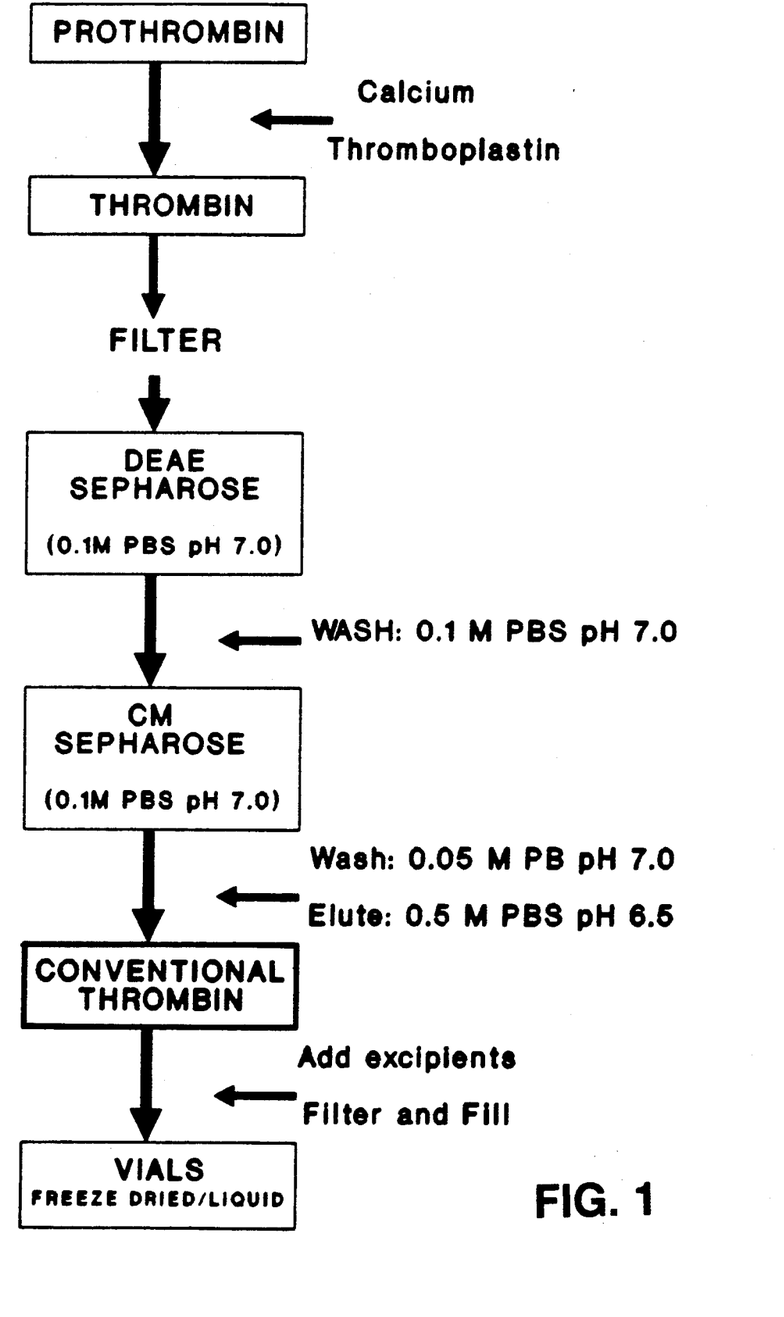
FIG. 1 is a schematic representation of a conventional process for the production of thrombin.

Conventionally thrombin has been prepared from bovine prothrombin derived from bovine plasma. The prothrombin is converted to thrombin using thromboplastin in the presence of calcium chloride. The thrombin thereby obtained is purified by passing filtered thrombin sequentially through an anion-exchange chromatography column and a cation-exchange chromatography column, followed by a one-step elution from the latter column. The process is depicted schematically in FIG. 1. The product thereby obtained has a specific activity of approximately 1,000 U/mg and exhibits a hazy appearance.

Problems exist with the conventional process due to the formation of insoluble salts on the chromatographic media. Removal of these salts requires routine washing with dilute acid. Frequent washing with acid significantly reduces the life of the media.

In the conventional process referred to herein, 10 units of thromboplastin (measured as N.I.H. units of thrombin produced) convert 1 unit of prothrombin (measured as N.I.H. units of thrombin produced) to 1 N.I.H. unit of thrombin, the concentrations of both thromboplastin and prothrombin being measured by an F.D.A.-approved assay for thrombin. This quanity of thromboplastin causes turbidity and increased protein load on the chromatographic media.

It is an object of the present invention to provide an improved and cost effective process for the production of thrombin which results in a thrombin preparation with increased specific activity relative to thrombin preparations obtained in conventional thrombin production.

It is a further object of the invention to provide a clear thrombin preparation relative to the hazy appearance of the conventional thrombin preparations.

It is a still further object of the invention to provide a thrombin preparation with high specific activity.

BRIEF SUMMARY OF THE INVENTION

A process for the preparation of liquid thrombin preparations with high specific activity and liquid thrombin preparations thereby obtained.

DETAILED DESCRIPTION OF THE INVENTION

Accordingly, the invention provides a process for the production of a liquid thrombin preparation, which process comprises reacting each unit of prothrombin (measured as N.I.H. units of thrombin produced) with less than 5 units of thromboplastin (measured as N.I.H. units of thrombin produced) in the presence of calcium, contacting the resultant thrombin with a phosphate buffer, diluting and filtering the suspension, applying the filtrate sequentially to an anion-exchange agarose column and a cation-exchange agarose column and step-wise eluting the thrombin fraction from the latter column with phosphate buffered saline.

The invention also provides a liquid thrombin preparation having a specific activity greater than 1,000 U/mg, (N.I.H. units/mg) more particularly greater than 1,600 U/mg.

In experiments carried out in connection with the present invention, it has been determined that thromboplastin as conventionally used in the preparation of thrombin may be diluted 1 in 20 while retaining its ability to activate prothrombin. When considered relative to the conventional process referred to above less than 5 units of thromboplastin convert 1 unit of prothrombin to thrombin in accordance with the invention. In the remainder of the specification when reference is made to the number of units of thromboplastin reacted with each unit of prothrombin, the number of units of thromboplastin will be based on the number of units used in the assay referred to above.

Preferably, the thromboplastin is diluted with a saline solution to between 20 and 40% (approximately 2–4 units) of the conventional thromboplastin input. In an especially preferred embodiment the amount of thromboplastin used is of the order of 30% (approximately 3 units) of the conventional input thereof.

The dilution of the thromboplastin reduces the protein load for purification.

The conversion of prothrombin to thrombin is suitably carried out in 5–40 mM calcium chloride solution at room temperature for a time of between 35 and 60 min.

Preferably the phosphate buffer (PB) is a 0.5–1.5M phosphate buffer at pH 6.0–7.0, added to achieve a final phosphate concentration of between 0.05 and 0.09M. In a particularly preferred embodiment the phosphate buffer used is a 1.0M phosphate buffer at pH 6.5, resulting in a final phosphate concentration of 0.07M. The treatment with phosphate buffer causes the calcium to precipitate out as calcium phosphate. As a result of this treatment precipitation of insoluble calcium salts is significantly reduced, eliminating the requirement to frequently wash the chromatographic media with 0.1M hydrochloric acid and thus extending the life of the media.

Suitably the anion exchange agarose material used is a fast flow Sepharose gel (Sepharose is a Trade Mark), especially one sold under the Trade Mark DEAE-Sepharose Fast Flow or Q-Sepharose Fast Flow. Likewise the cation exchange agarose material used is suitably a fast flow Sepharose gel, especially one sold under the Trade Mark CM-Sepharose Fast Flow or S-Sepharose Fast Flow.

Preferably, a two-step elution with phosphate buffered saline (PBS) at pH 6.0-7.0 is used to elute the thrombin from the cation exchange column. Thus in a preferred embodiment the column is eluted first with 0.16-0.18M, more especially 0.17M, phosphate buffered saline at pH 6.5 and it is then eluted with 0.26-0.30M, more especially 0.28M, phosphate buffered saline at pH 6.5.

The first step of the step-wise elution removes contaminating protein material and the second step of the elution yields a highly purified thrombin preparation.

Apart from the step involving conversion of prothrombin to thrombin, the process according to the invention is carried out at a temperature in the range $2°-8°$ C.

The purity of the product obtained in accordance with the invention is also confirmed by electrophoresis as hereinafter described.

The bulk thrombin product obtained in accordance with the process of the invention is suitably mixed with excipients, filtered and filled into vials under aseptic conditions.

By the term "thrombin preparation(s)" as used here is contemplated all types of formulations in which thrombin, in liquid or freeze-dried form, is present in combination with one or more glycols, buffers and other excipients.

Liquid thrombin preparations in accordance with the invention remain stable at room temperature for periods in excess of six months. When mixed with stabilizing quantities of buffers of the type specified in U.S. Pat. Nos. 4,696,812 and 4,965,203, such liquid thrombin preparations are found to retain 100% of their original clotting activity after storage at room temperature for six months. The initial clotting activity of the thrombin preparations in accordance with the invention is at least 1,000 units/ml.

Thus, liquid thrombin preparations obtained in accordance with the invention are characterised by being clear and free of haziness, by having a high and sustainable clotting activity, by being substantially free of calcium, by having a high specific activity which is typically greater than 1,600 U/mg.

The liquid thrombin preparations in accordance with the invention may be used with conventional haemostatic materials such as AVICEL, GELFOAM, SURGICEL and collagen (AVICEL, GELFOAM and SURGICEL are Trade Marks).

The thrombin preparations in accordance with the invention may, for example, be adsorbed onto the haemostatic material and the resultant product freeze-dried.

The thrombin preparations in accordance with the invention may also include one or more antimicrobial agent(s), especially when contemplated for use in the treatment of burns.

The thrombin preparations in accordance with the invention may also be freeze-dried.

The invention will be further illustrated by the following Example.

EXAMPLE

Preparation of thromboplastin 115 kg of fresh bovine lungs were washed, minced and suspended in 0.9% sodium chloride at 1° to 5° C. for up to 48 h. with continuous mixing. The suspension was centrifuged and the effluent treated with magnesium hydroxide and again centrifuged. The thromboplastin was extracted from the effluent by twice treating it with ammonium sulphate. The final precipitate was resolubilized in 20 l. of 0.9% sodium chloride, dialysed against water and concentrated to approximately 9 l. by ultrafiltration. The final volume was adjusted to 11 l. by adding sodium chloride to a final concentration of 0.9%, and frozen.

When required, the thromboplastin was thawed and diluted approximately 1 in 3 with 0.9% sodium chloride.

Preparation of thrombin

Bovine prothrombin 280 million units (MMU) was reacted with diluted thromboplastin (840 MMU) in the presence of 9 mM calcium chloride solution at a temperature of 25° C. for 60 min. Approximately 6 l. of 1.0M phosphate buffer at pH 6.5 was added to the solution, chilled, and held for a minimum of 15 min. The suspension was further diluted to approximately 0.07M phosphate and then filtered down to 5 μm and the filtrate loaded on a DEAE Sepharose Fast Flow anion exchange column in 0.1M phosphate buffered saline at pH 6.5 and the partially purified thrombin eluted with the same buffer.

The eluant was then loaded on a CM-Sepharose Fast Flow cation exchange column in 0.1M PBS at pH 6.5. The column was then step-wise eluted with 0.17M PBS, to elute non-thrombin proteins, followed by 0.28M PBS which eluted the pure thrombin.

Figure 3:
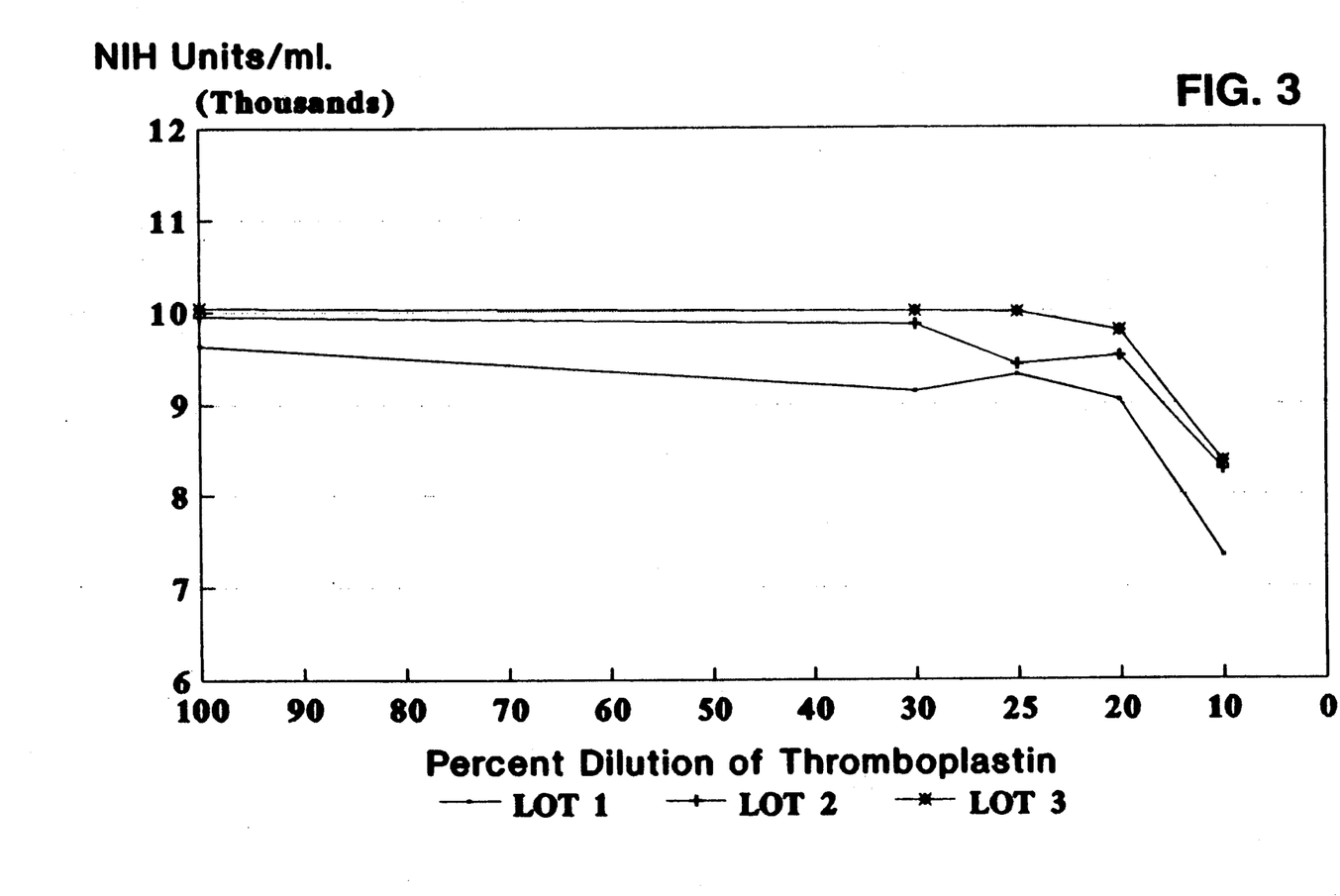
FIG. 3 is a plot of units of prothrombin converted to thrombin (NIH (National Institute of Health) Units/ml (thousands)) versus percent dilution of thromboplastin.

FIG. 3 depicts the effect of diluting the conventional quantity of thromboplastin on its ability to convert prothrombin to thrombin for three different lots of thromboplastin.

Figure 4:
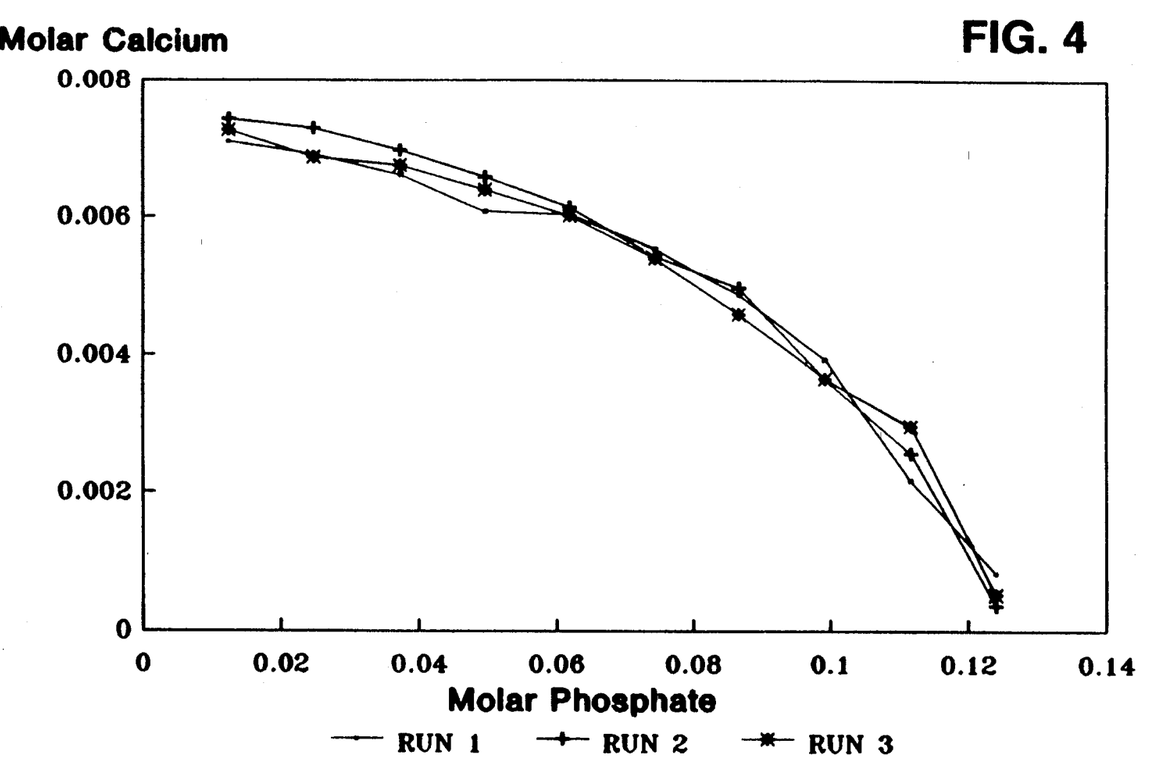
FIG. 4 is a plot of calcium depletion (M) versus phosphate addition (M) prior to the filtration step in the process according to the invention.

The removal of calcium by means of calcium phosphate precipitation prior to the filtration step is depicted in FIG. 4 and shows the results for three different runs.

Figure 2:
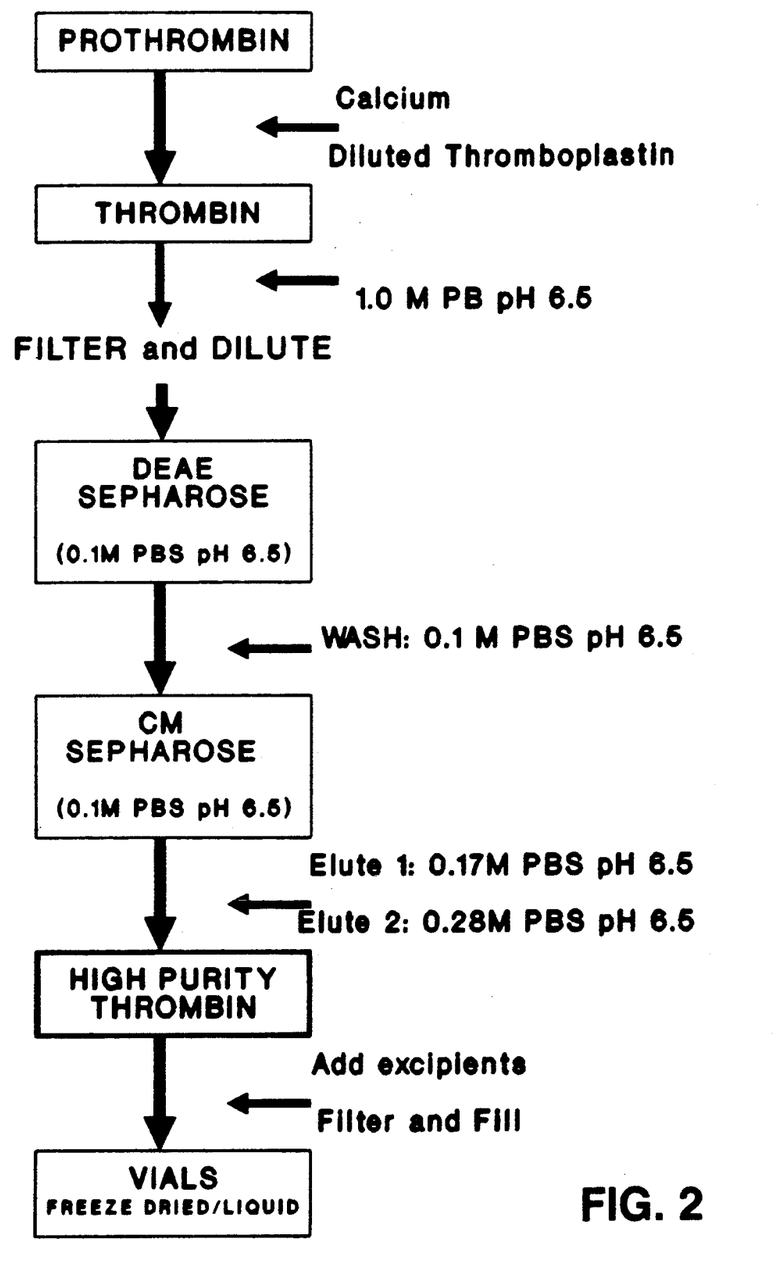
FIG. 2 is a schematic representation of an embodiment of the process in accordance with the invention for the production of thrombin.
Figure 6:
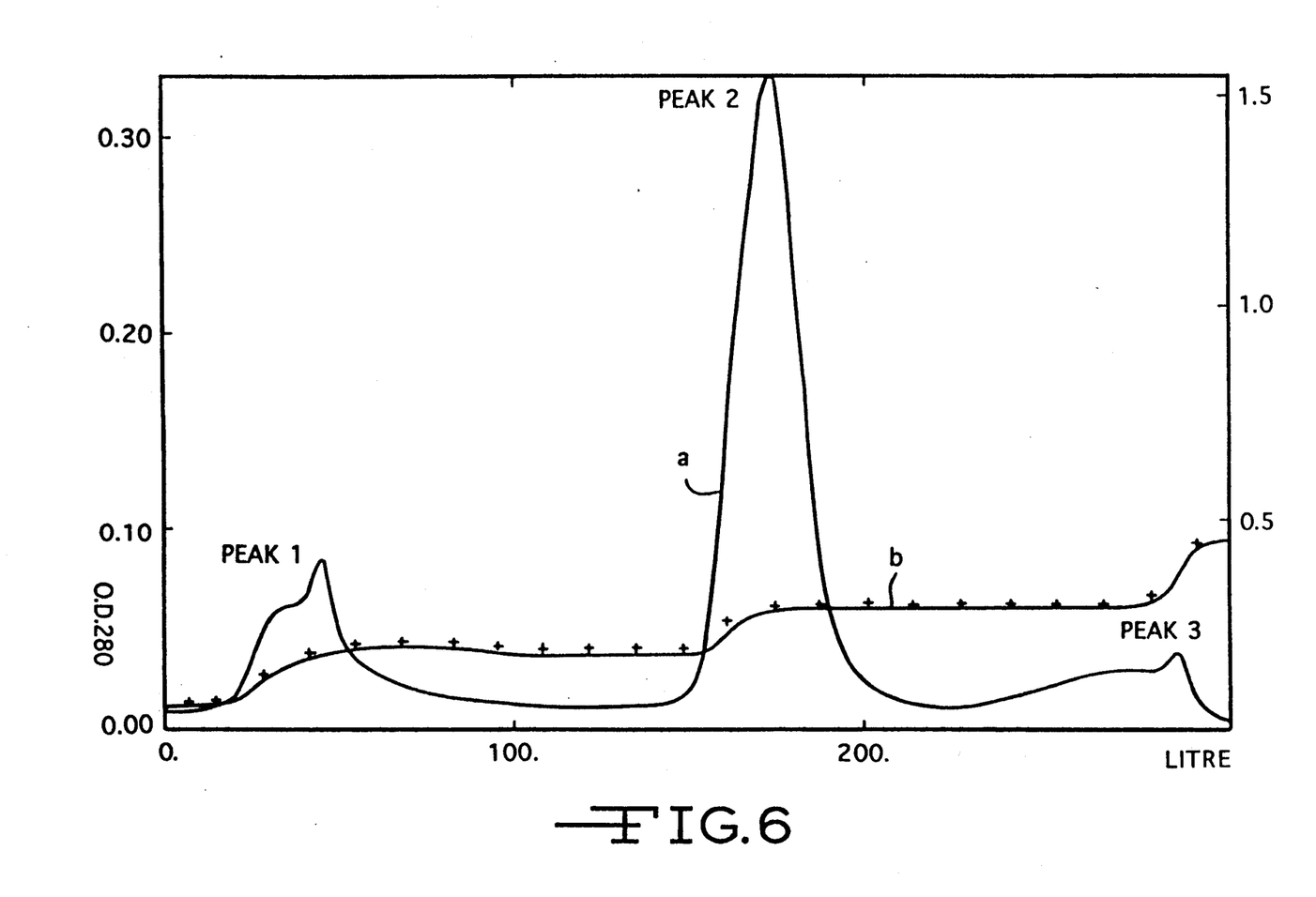
FIG. 6 is a plot of optical density at 280 nm versus eluate volume for the step-wise elution from the cation exchange column in accordance with the process depicted in FIG. 2.

The overall process is depicted schematically in FIG. 2 and the step-wise elution of the CM-Sepharose column is depicted in FIG. 6.

Figure 5:
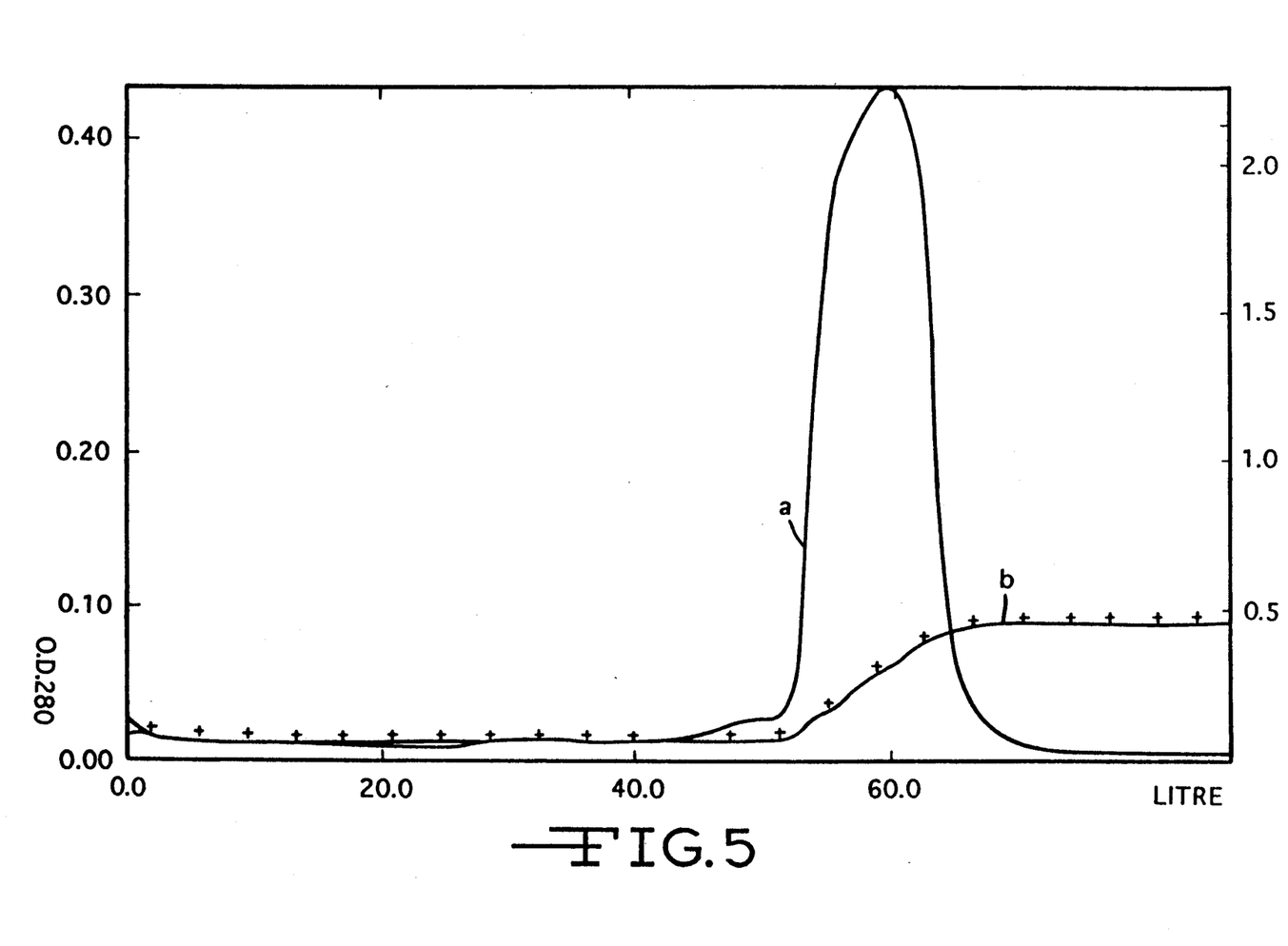
FIG. 5 is a plot of optical density at 280 nm versus eluate volume for the one-step elution from the cation exchange column in accordance with the process depicted in FIG. 1.

As indicated in FIG. 6 a third inactive peak can be eluted using 0.5M PBS. In the conventional process the active thrombin peak (peak 2) plus the two peaks of contaminating material (peaks 1 and 3) are eluted as a single fraction using 0.5M PBS. Thus FIG. 6 indicates three peaks relative to the single peak of FIG. 5 representative of the conventional process. That the major peak of FIG. 6 represents thrombin and the minor peaks non-active protein material is determined by a measurement of thrombin clotting activity using a fibrometer. In each of FIGS. 5 and 6 curve a represents optical density (O.D.) and curve b represents ionic concentration in moles/liter.

Figure 7:
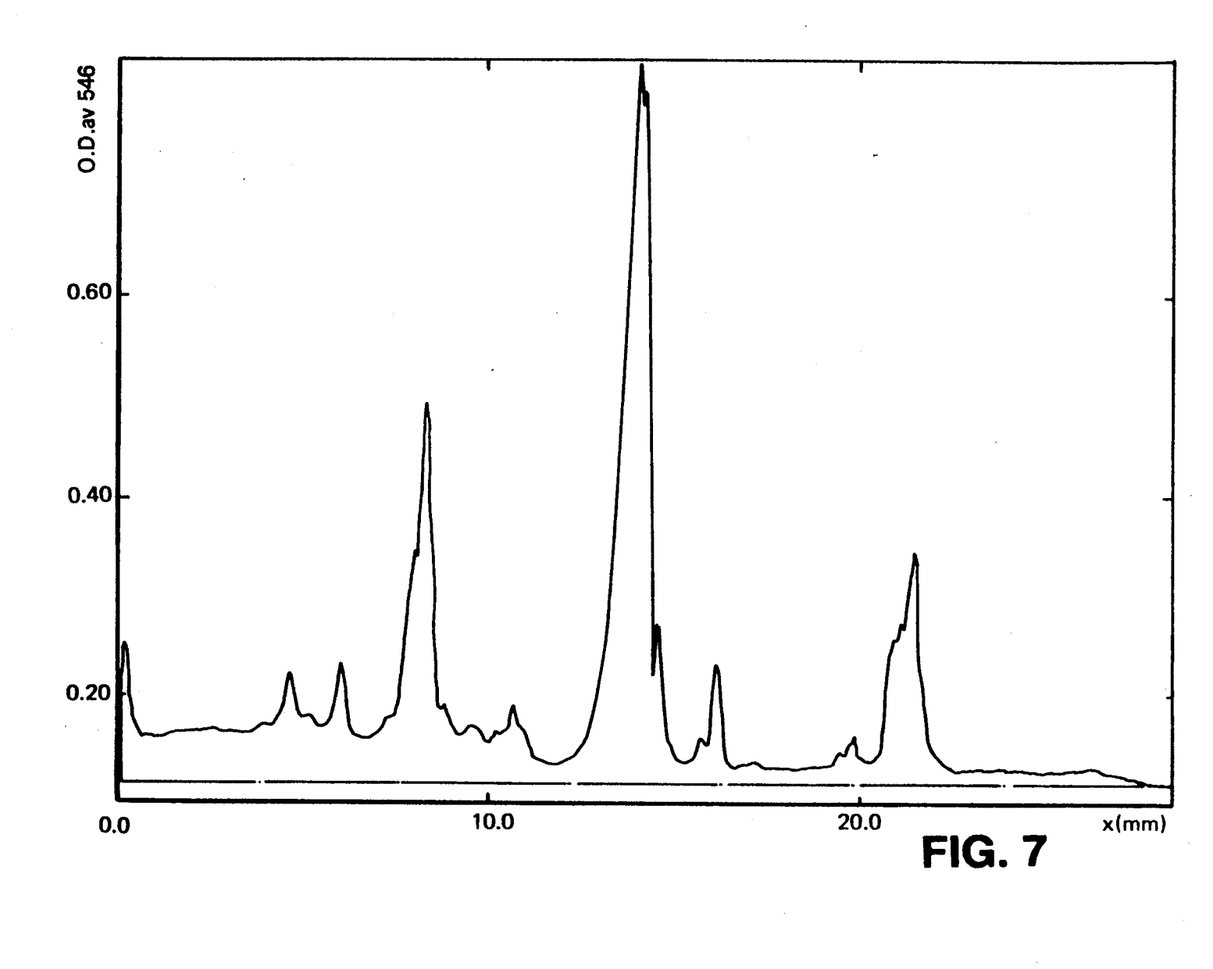
FIG. 7 is a plot of O.D. at 546 nm versus distance migrated (mm) from the point of application following electrophoresis using SDS-PAGE for a thrombin sample prepared in accordance with the conventional process depicted in FIG. 1.
Figure 8:
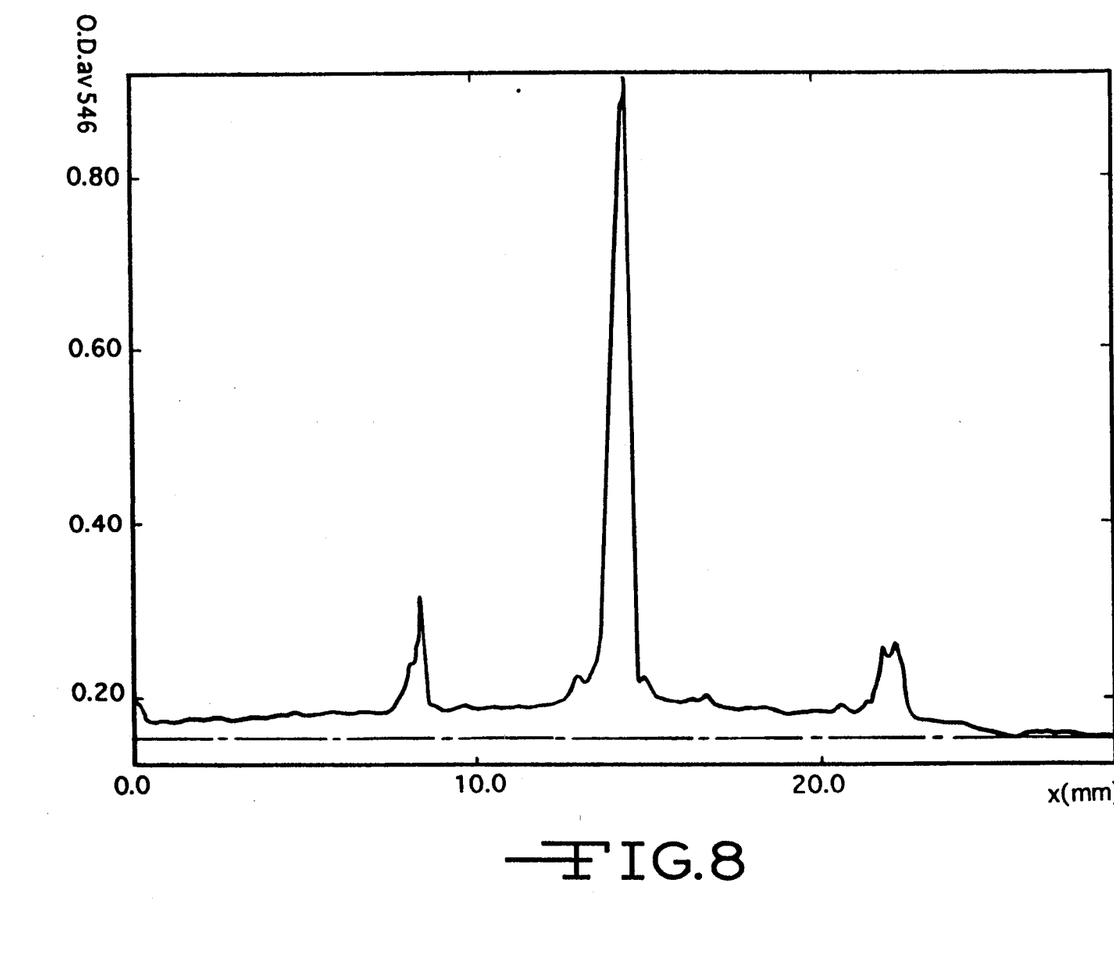
FIG. 8 is a plot of O.D. at 546 nm versus distance migrated (mm) from the point of application following electrophoresis using SDS-PAGE for a sample prepared in accordance with the invention as described in the Example.

Thrombin prepared in accordance with the conventional process (FIG. 1) and in accordance with the process according to the invention (FIG. 2) were subjected to polyacrylamide gel electrophoresis with SDS (SDS-PAGE) and the results are shown in FIG. 7 and FIG. 8, respectively.

Both products were subjected to the same dilution to 1,000 units/ml for characterization by molecular weight by the SDS-PAGE using an automated electrophosesis and development system marketed by Pharmacia under the Trade Mark PHASTSYSTEM using PHASTGEL (TRADE MARK) polyacrylamide gels. After separation the gels were transferred to the development unit of the system, stained using the silver stain technique and air dried overnight.

A Phast Image (Trade Mark) densitometer was used to scan the gels at 546 nm in the transmittance mode and a plot of O.D. versus distance migrated along the gel was obtained for each sample (FIGS. 7 and 8). 546 nm is optimal for use with silver stained gels.

In the case of each of FIGS. 7 and 8 the main central peak represents active thrombin shown to have a molecular weight of 32,000.

The specific activity of thrombin prepared in accordance with the invention was compared with that obtained by the conventional process. In each case the specific activity of three separate lots of thrombin was determined. The results are shown in the following Table.

TABLE

| Sample No. | Specific Activity of Thrombin Preparations (Units/mg) | |
|---|---|---|
| | Conventional Product | Product according to the invention |
| 1 | 1376 | 2279 |
| 2 | 1212 | 1929 |
| 3 | 1517 | 1950 |
| | Av. 1368 | Av. 2053 |

What we claim is:

1. A process for the production of a liquid thrombin preparation, which process comprises reacting each unit of prothrombin measured as N.I.H. units of thrombin produced, with less than 5 units of thromboplastin, measured as N.I.H. units of thrombin produced, in the presence of calcium to produce thrombin contacting the resultant thrombin with a phosphate buffer to produce a suspension diluting and filtering the suspension to produce a filtrate applying the filtrate sequentially to an anion-exchange agarose column and a cation-exchange agarose column and step-wise eluting a thrombin fraction from the cation-exchange column with phosphate buffered saline.

2. A process according to claim 1, wherein the amount of thromboplastin used is between 2 and 4 units.

3. A process according to claim 1, wherein the amount of thromboplastin used is of the order of 3 units.

4. A process according to claim 1, wherein the phosphate buffer used is a 0.5–1.5M phosphate buffer at pH 6.0–7.0.

5. A process according to claim 1, wherein the phosphate buffer used is a 1.0M phosphate buffer at pH 6.5.

6. A process according to claim 1, wherein the step-wise elution of the cation exchange agarose column is a two-step elution.

7. A process according to claim 1, wherein the cation exchange agarose column is sequentially eluted with i) 0.16–0.18M phosphate buffered saline and ii) 0.26–0.30M phosphate buffered saline.

8. A process according to claim 1, wherein the cation exchange agarose column is sequentially eluted with i) 0.17M phosphate buffered saline and ii) 0.28M phosphate buffered saline.

* * * * *